US006858607B1

(12) United States Patent
Cai et al.

(10) Patent No.: US 6,858,607 B1
(45) Date of Patent: Feb. 22, 2005

(54) 7,8-FUSED 4H-CHROMENE AND ANALOGS AS ACTIVATORS OF CASPASES AND INDUCERS OF APOPTOSIS AND THE USE THEREOF

(75) Inventors: Sui Xiong Cai, San Diego, CA (US); Lifen Xu, San Diego, CA (US); Richard Storer, Pinner (GB); Giorgio Attardo, Laval (CA)

(73) Assignee: Cytovia, Inc., San Diego, CA (US)

( * ) Notice: Subject to any disclaimer, the term of this patent is extended or adjusted under 35 U.S.C. 154(b) by 105 days.

(21) Appl. No.: 10/146,139

(22) Filed: May 16, 2002

Related U.S. Application Data

(60) Provisional application No. 60/290,976, filed on May 16, 2001.

(51) Int. Cl.[7] .................... A61K 31/437; C07D 471/04
(52) U.S. Cl. .................... 514/229.8; 514/250; 514/359; 514/362; 514/366; 514/375; 514/388; 514/394; 544/101; 544/345; 548/126; 548/151; 548/218; 548/256; 548/257; 548/260; 548/302.1
(58) Field of Search ...................... 544/101, 345; 548/126, 151, 218, 256, 257, 260, 302.1; 514/229.8, 250, 359, 362, 366, 375, 388, 394

(56) References Cited

U.S. PATENT DOCUMENTS

| | | | |
|---|---|---|---|
| 3,989,816 | A | 11/1976 | Rajadhyaksha |
| 4,444,762 | A | 4/1984 | Rajadhyaksha |
| 5,281,619 | A | 1/1994 | Dell et al. |
| 5,284,868 | A | 2/1994 | Dell et al. |
| 5,434,160 | A | 7/1995 | Dell et al. |
| 5,514,706 | A | 5/1996 | Ambler et al. |
| 5,571,818 | A | 11/1996 | Williams |
| 5,574,034 | A | 11/1996 | Williams |
| 5,576,325 | A | 11/1996 | Williams |
| 5,624,953 | A | 4/1997 | Ambler et al. |
| 5,637,589 | A | 6/1997 | Lee et al. |
| 5,726,204 | A | 3/1998 | Lee et al. |
| 5,847,165 | A | 12/1998 | Lee et al. |
| 6,160,010 | A | 12/2000 | Uckun et al. |
| 6,221,900 | B1 | 4/2001 | Uckun et al. |
| 6,258,824 | B1 | 7/2001 | Yang |
| 6,294,575 | B1 | 9/2001 | Uckun et al. |
| 6,303,652 | B1 | 10/2001 | Uckun et al. |
| 6,335,429 | B1 | 1/2002 | Cai et al. |
| 6,365,626 | B1 | 4/2002 | Uckun et al. |
| 6,388,092 | B2 | 5/2002 | Yang |

FOREIGN PATENT DOCUMENTS

| | | |
|---|---|---|
| EP | 0 537 949 A1 | 4/1993 |
| EP | 0 599 514 A2 | 6/1994 |
| EP | 0 618 206 A1 | 10/1994 |
| EP | 0 619 314 A1 | 10/1994 |
| WO | WO 98/24427 | 6/1998 |
| WO | WO 99/54286 | 10/1999 |
| WO | WO 01/34591 A2 | 5/2001 |

OTHER PUBLICATIONS

A1–Mousawi, S.M., et al., "Synthesis of New Condensed 2–Amino–4H–Pyran–3–Carbonitriles and of 2–Aminoquinoline–3–Carbonitriles," *Organic Preparations and Procedures Int.* 31:305–313, Organic Preparations and Procedures Inc. (1999).

Batteux, F., et al., "Gene Therapy of Experimental Autoimmune Thyroiditis by In Vivo Administration of Plasmid DNA Coding for Fas Ligand," *J. Immunol.* 162:603–608, The American Association of Immunologists (1999).

Birch, K.A., et al., "LY290181, an Inhibitor of Diabetes–Induced Vascular Dysfunction, Blocks Protein Kinase C–Stimulated Transcriptional Activation Through Inhibition of Transcription Factor Binding to a Phorbol Response Element," *Diabetes* 45:642–650, American Diabetes Association (1996).

Bloxham, J., et al., "Preparation of Some New Benzylidenemalononitriles by an $S_NAr$ Reaction: Application to Naphtho[1,2–b] pyran Synthesis." *Heterocycles* 38:399–408, The Japan Institute of Heterocyclic Chemistry (1994).

Boirivant, M., et al., "Lamina Propria T Cells in Crohn's Disease and Other Gastrointestinal Inflammation Show Defective CD2 Pathway–Induced Apoptosis," *Gastroenterology* 116:557–565, The American Gastroenterological Association (1999).

(List continued on next page.)

Primary Examiner—Richard L. Raymond
(74) Attorney, Agent, or Firm—Sterne, Kessler, Goldstein & Fox P.L.L.C.

(57) ABSTRACT

The present invention is directed to substituted 4H-chromene and analogs thereof, represented by the general Formula I:

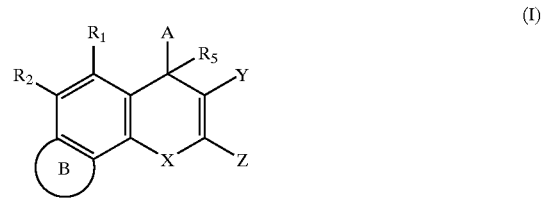

(I)

or pharmaceutically acceptable salts or prodrugs thereof, wherein:
wherein A, $R_1$, $R_2$, $R_5$, X, Y, and Z, are defined herein and B is a fused thiazole, oxazole, 2-imino-imidazole, 2,1,3-thiadiazo-2-one, thiazol-2-one, oxazol-2-one, imidazol-2-thione, thiazol-2-thione, oxazol-2-thione, imidazoline, oxazoline, thiazoline, triazole, oxazine, oxazine-2,3-dione, or piperazine ring. The present invention also relates to the discovery that compounds having Formula I are activators of caspases and inducers of apoptosis. Therefore, the activators of caspases and inducers of apoptosis of this invention can be used to induce cell death in a variety of clinical conditions in which uncontrolled growth and spread of abnormal cells occurs.

36 Claims, No Drawings

OTHER PUBLICATIONS

Chandrasekhar, S., et al., "Indentification of a Novel Chemical Series That Blocks Interleukin–1–Stimulated Metalloprotease Activity in Chrondrocytes," *J. Pharmacol. Exp. Ther.* 273:1519–1528, The American Society for Pharmacology and Experimental Therapeutics (1995).

Sharanin, Y.A., and Klokol, G.V., "Synthesis of 2–amino–4H–chromenes," Chemical Abstracts, vol. 99, No. 27, Abstract No. 212393z, American Chemical Society (1983).

Wiernicki, T.R., et al., "Inhibition of vascular smooth muscle cell proliferation and arterial intimal thickening by a novel antiproliferative naphthopyran," Chemical Abstracts, vol. 125, No. 21, Abstract No. 265467p, American Chemical Society (1996).

Coven, T.R., et al., "PUVA–induced lymphocyte apoptosis: Mechanism of action in psoriasis," *Photodermatol. Photoimmunol. Photomed.* 15:22–27, Munksgaard (1999).

Elagamey, A.G.A., et al., "Nitriles in Heterocyclic Synthesis: Novel Syntheses of Benzo[b] pyrans, Naphtho [1,2–b] pyrans, Naphtho [2,1–b] pyrans, Pyrano [3,2–h] quinolines and Pyrano [3,2–c] quinolines," *Collection Czechoslovak. Chem. Commun.* 53:1534–1538, Institute of Organic Chemistry and Biochemistry (1988).

Friesen, C., et al., "Involvement of the CD95 (APO–1/Fas) receptor/ligand system in drug–induced apoptosis in leukemia cells," *Nat. Med.* 2:574–577, Nature Publishing Co. (1996).

Greenwald, R.B., "Drug Delivery Systems Employing 1,4— or 1, 6–Elimination: Poly (ethylene glycol) Prodrugs of Amine–Containing Compounds," *J. Med. Chem.* 42:3657–3667, American Chemical Society (1999).

Heenen, M., et al., "Methotrexate induces apoptotic cell death in human keratinocytes," *Arch. Dermatol. Res.* 290:240–245, Springer–Verlag (1998).

Infante, A.J., et al., "The clinical spectrum in a large kindred with autoimmune lymphoproliferative syndrome caused by a Fas mutation that impairs lymphocyte apoptosis," *J. Pediatr.* 133:629–633, Mosby, Inc. (1998).

International Search Report for International Application No. PCT/US 02/15398, mailed Oct. 25, 2002.

Klokol, G.V., et al., "Cyclization of Nitriles. XXIII. Addition of Active Phenols to Electron–Deficient Ethylenes, Accompanied by Cyclization to 2–Amino–4H–benzo[b]pyrans. Crystal Structure of 2–Amino–4–(2–Fluorophenyl)–3–Ethoxycarbonyl–4H–Naphtho[2,1–b]pyran" *J. Org. Chem. USSR* 23:369–377, Plenum Publishing Corporation (1987).

Leu, Y.–L., et al., "Design and Synthesis of Water–Soluble Glucuronide Derivatives of Camptothecin for Cancer Prodrug Monotherapy and Antibody–Directed Enzyme Prodrug Therapy (ADEPT)," *J. Med. Chem.* 42:3623–3628, American Chemical Society (1999).

López–Hoyos, M., et al., "Regulation of B cell apoptosis by Bcl–2 and Bcl–$X_L$ and its role in the development of autoimmune diseases (Review)," *Int. J. Mol. Med.* 1:475–483, D.A. Spandidos (1998).

Los, M., et al., "Cross–Resistance of CD95– and Drug–Induced Apoptosis as a Consequence of Deficient Activation of Caspases (ICE/Ced–3 Proteases)," *Blood* 90:3118–3129, The American Society of Hematology (1997).

McCarty, M.F., "Polyphenol–mediated inhibition of AP–1 transactivating activity may slow cancer growth by impeding angiogenesis and tumor invasiveness." *Med. Hypotheses* 50:511–514, Harcourt Brace & Co. Ltd. (1998).

O'Reilly, L.A., and Strasser, A., "Apoptosis and autoimmune disease," *Inflamm. Res.* 48:5–21, Birkhauser Verlag (1999).

Ohsako, S., and Elkon, K.B., "Apoptosis in the effector phase of autoimmune diabetes, multiple sclerosis and thyroiditis," *Cell Death Differ.* 6:13–21, Stockton Press (1999).

Orrenius, S., "Apoptosis: molecular mechanisms and implications for human disease," *J. Int. Med.* 237:529–536, Blackwell Science Ltd. (1995).

Ozawa, M., et al., "312–nanometer Ultraviolet B Light (Narrow–Band UVB) Induces Apoptosis of T Cells within Psoriatic Lesions," *J. Exp. Med.* 189:711–718, The Rockefeller University Press (1999).

Panda, D., et al., "Suppression of Microtubule Dynamics by LY2910181, a Potential Mechanism for Its Antiproliferative Action," *J. Biol. Chem.* 272:7681–7687, The American Society for Biochemistry and Molecular Biology, Inc. (1997).

Paull, K.D., et al., "Identification of Novel Antimitotic Agents Acting at the Tubulin Level by Computer–assisted Evaluation of Differential Cytotoxicity Data," *Cancer Res.* 52:3892–3900, American Association for Cancer Research, Inc. (1992).

Cai et al., Pending Non–Provisional U.S. Appl. No. 09/705, 840, filed Nov. 6, 2000 (not published).

Cai et al., Pending Non–Provisional U.S. Appl. No. 10/146, 138, filed May 16, 2002 (not published).

Cai et al., Pending Non–Provisional U.S. Appl. No. 10/146, 136, filed May 16, 2002 (not published).

Radwan, S.M., et al., "Synthesis and Some Reactions of New Benzo [b] pyran Derivatives," *Phosphorus, Sulfur, and Silicon* 101:207–211, Gordon and Breach Science Publishers SA (1995).

Ruddon, R.W., "Biochemistry of Cancer," in *Cancer Medicine*, 5$^{th}$ edition, Gansler, T.S., ed., American Cancer Society, Inc., Atlanta, GA, pp. 108–120 (2000).

Savill, J., "Apoptosis in resolution of inflammation," *J. Leukoc. Biol.* 61:375–380, The Society for Leukocyte Biology (1997).

Schmitt, E., et al., "The Bcl–xL and Bax–α control points: modulation of apoptosis induced by cancer chemotherapy and relation to TPCK–sensitive protease and caspase activation," *Biochem. Cell Biol.* 75:301–314, National Research Council of Canada (1997).

Sharanin, Yu.A., and Klokol, G.V., "Synthesis of 2–Amino–4H–Chromenes," *J. Org. Chem. USSR* 19:1582–1583, Plenum Publishing Corporation (1983).

Smith, C.W., et al., "The Anti–Rheumatic Potential of a Series of 2,4–Di–Substituted–4H–Naphtho [1,2–b] pyran–3–Carbonitriles," *Bioorg. Med. Chem. Lett.* 5:2783–2788, Elsevier Science Ltd. (1995).

Vaishnaw, A.K., et al., "The molecular basis for apoptotic defects in patients with CD95 (Fas/Apo–1) mutations," *J. Clin. Invest.* 103:355–363, The American Society for Clinical Investigation (1999).

Wakisaka, S., et al., "Modulation by proinflammatory cytokines of Fas/Fas ligand–mediated apoptotic cell death of synovial cells in patients with rheumatoid arthritis (RA)," *Clin. Exp. Immunol.* 114:119–128, Blackwell Science (1998).

Wiernicki, T.R., et al., "Inhibition of Vascular Smooth Muscle Cell Proliferation and Arterial Intimal Thickening by a Novel Antiproliferative Naphthopyran," *J. Pharmacol. Exp. Ther.* 278:1452–1459, The American Society for Pharmacology and Experimental Therapeutics (1996).

Wood, D.L., "Inhibition of Mitosis and Microtubule Function through Direct Tubulin Binding by a Novel Antiproliferative Naphthopyran LY290181," *Mol. Pharmacol.* 52:437–444, The American Society for Pharmacology and Experimental Therapeutics (1997).

Zhou, T., et al., "Bisindolylmaleimide VIII facilitates Fas–mediated apoptosis and inhibits T cell–mediated autoimmune diseases," *Nat. Med.* 5:42–48, Nature Publishing Co. (1999).

7,8-FUSED 4H-CHROMENE AND ANALOGS AS ACTIVATORS OF CASPASES AND INDUCERS OF APOPTOSIS AND THE USE THEREOF

REFERENCE TO RELATED APPLICATIONS

The present application claims the benefit of the filing date of U.S. provisional application No. 60/290,976, filed May 16, 2001.

BACKGROUND OF THE INVENTION

1. Field of the Invention

This invention is in the field of medicinal chemistry. In particular, the invention relates to 7,8-fused 4H-chromene and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death, or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis, et al., *Dev.* 112:591–603 (1991); Vaux, et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995).

It has been found that a group of proteases are a key element in apoptosis (see, e.g., Thornberry, *Chemistry and Biology* 5:R97–R103 (1998); Thornberry, *British Med. Bull.* 53:478–490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal and cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118–3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_0$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g., colon cancers, exist primarily in the $G_0$ phase, whereas rapidly proliferating normal tissues, e.g., bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP537949 discloses derivatives of 4H-naphtho[1,2-b] pyran as antiproliferatives:

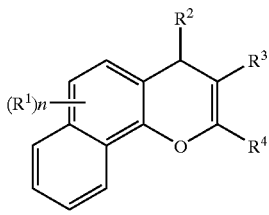

wherein,
each $R^1$ is independently halo, trifluoromethyl, $C_{1-4}$ alkoxy, hydroxy, nitro, $C_{1-4}$ alkyl, $C_{1-4}$ alkylthio, hydroxy-$C_{1-4}$alkyl, hydroxy-$C_{1-4}$alkoxy, trifluoro-methoxy, carboxy, —COOR$^5$ where $R^5$ is an ester group, —CONR$^6$R$^7$ or —NR$^6$R$^7$ where $R^6$ and $R^7$ are each hydrogen or $C_{1-4}$ alkyl;
$R^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or $R^2$ is furanyl optionally substituted with $C_{1-4}$ alkyl;
$R^3$ is nitrile, carboxy, —COOR$^8$ where $R^8$ is an ester group, —CONR$^9$R$^{10}$ where $R^9$ and $R^{10}$ are each hydrogen or $C_{1-4}$ alkyl or $R^{11}$SO$_2$ where $R^{11}$ is $C_{1-4}$ alkyl or optionally substituted phenyl;
$R^4$ is —NR$^{12}$R$^{13}$, —NHCOR$^{12}$, —N(COR$^{12}$)$_2$ or —N=CHOCH$_2$R$^{12}$ where $R^{12}$ and $R^{13}$ are each hydrogen or $C_{1-4}$ alkyl optionally substituted with carboxy, or $R^4$ is

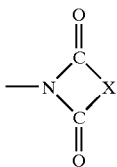

where X is $C_{2-4}$ alkylene, or $R^4$ is —NHSO$_2$R$^{14}$ where $R^{14}$ is $C_{1-4}$ alkyl or optionally substituted phenyl; and
n is 0–2.

U.S. Pat. No. 5,281,619 discloses naphthopyrans for therapy of diabetic complications:

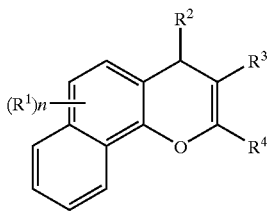

wherein,
$R^1$ is $C_{1-4}$ alkoxy, OH or COOH;
$R^2$ is optionally substituted phenyl;
$R^3$ is nitrile, or $R^3$ is carboxy or —COOR$^8$ when $R^2$ is phenyl substituted with 3-nitro or 3-trifluoromethyl and $R^8$ is an ester group;

$R^4$ is NR$^{12}$R$^{13}$, —NHCOR$^{12}$, —N(COR$^{12}$)$_2$ or —N=CHOCH$_2$R$^{12}$, wherein $R^{12}$ and $R^{13}$ are each H or $C_{1-4}$ alkyl; and
n is 0–2.

EP599514 discloses the preparation of pyranoquinoline derivatives as inhibitors of cell proliferation:

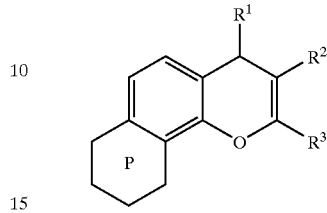

wherein $R^1$ is optionally substituted phenyl or optionally substituted heteroaryl selected from thienyl, pyridyl, benzothienyl, quinolinyl, benzofuranyl or benzimidazolyl, or $R^1$ is furanyl optionally substituted with $C_{1-4}$ alkyl;
$R^2$ is nitrile, carboxy, —CO$_2$R$^4$ wherein $R^4$ is an ester group, —CON(R$^5$)R$^6$ where $R^5$ and $R^6$ are independently H or $C_{1-4}$ alkyl, or $R^7$SO$_2$ where $R^7$ is $C_{1-4}$ alkyl or optionally substituted phenyl;
$R^3$ is —NR$^8$R$^9$, —NHCOR$^8$, —N(CO$_2$R$^8$)$_2$, —N=CHOR$^8$ where $R^8$ and $R^9$ are independently H or $C_{1-4}$ alkyl, or —NHSO$_2$R$^{10}$ where $R^{10}$ is $C_{1-4}$ alkyl or optionally substituted phenyl, or

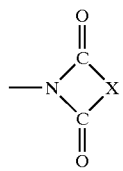

where X is $C_{2-4}$ alkylene; and
the ring P represents a pyridine fused to the benzopyran nucleus.

EP618206 discloses the preparation of naphthopyran and pyranoquinoline as immunosuppressants and cell proliferation inhibitors:

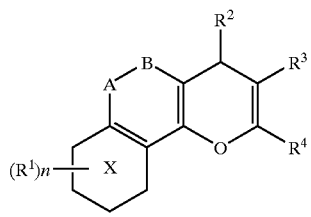

wherein,
A—B is CH$_2$CH$_2$ or CH=CH;
each $R^1$ is independently halo, carboxy, trifluoromethyl, hydroxy, $C_{1-4}$ alkyl, $C_{1-4}$ alkoxy, $C_{1-4}$ alkylthio, hydroxy-$C_{1-4}$alkyl, hydroxy-$C_{1-4}$alkoxy, nitrogen-containing heterocyclyl, nitro, trifluoromethoxy, —COOR$^5$ where $R^5$ is an ester group, —COR$^6$, —CONR$^6$R$^7$ or —NR$^6$R$^7$ where $R^6$ and $R^7$ are each hydrogen or $C_{1-4}$alkyl;
$R^2$ is phenyl, napthyl or heteroaryl selected from thienyl, pyridyl, benzothienyl, quinolinyl, benzofuranyl or benzimidazolyl, wherein said phenyl, napthyl and heteroaryl groups are optionally substituted, or $R^2$ is furanyl optionally substituted with $C_{1-4}$ alkyl;

$R^3$ is nitrile, carboxy, —COOR$^8$ where R$^8$ is an ester group, —CONR$^9$R$^{10}$ where $R^9$ and $R^{10}$ are each hydrogen or $C_{1-4}$ alkyl, or —SO$_2$R$^{11}$ where $R^{11}$ is $C_{1-4}$ alkyl or optionally substituted phenyl-$C_{1-4}$ alkyl;

$R^4$ is 1-pyrrolyl, 1-imidazolyl or 1-pyrazolyl, each of which is optionally substituted by one or two $C_{1-4}$ alkyl, carboxyl, hydroxyl-$C_{1-4}$alkyl or —CHO groups, or $R^4$ is 1-(1,2,4-triazolyl), 1-(1,3,4-triazolyl) or 2-(1,2,3-triazolyl), each of which is optionally substituted by a $C_{1-4}$ alkyl or $C_{1-4}$ perfluoroalkyl group, or $R^4$ is 1-tetrazolyl optionally substituted by $C_{1-4}$ alkyl;

X is a pyridine or a benzene ring; and n is 0–2.

EP619314 discloses the preparation of 4-phenyl-4H-naphtho(2,1-b)-pyran derivatives:

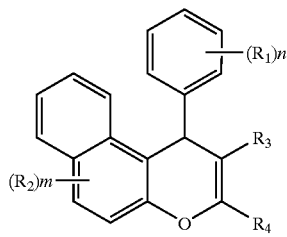

wherein,

R$_1$ and R$_2$ are independently halo, trifluoromethyl, $C_1$–$C_4$ alkoxy, hydroxy, nitro, $C_1$–$C_4$ alkyl, $C_1$–$C_4$ alkylthio, hydroxy-$C_1$–$C_4$ alkyl, hydroxy-$C_1$–$C_4$ alkoxy, trifluoromethoxy, carboxy, —COOR$_8$ where R$_8$ is an ester group, —COR$_9$, —CONR$_9$R$_{10}$ or —NR$_9$R$_{10}$ where R$_9$ and R$_{10}$ are each hydrogen or $C_1$–$C_4$ alkyl;

R$_3$ is nitrile, carboxy or —CO$_2$R$_{11}$ wherein R$_{11}$ is an ester group;

R$_4$ is —NR$_{12}$R$_{13}$, —NR$_{12}$COR$_{13}$, —N(COR$_{12}$)$_2$ or —N=CHOCH$_2$R$_{12}$ where R$_{12}$ and R$_{13}$ are each hydrogen or $C_{1-4}$ alkyl, or R$_4$ is

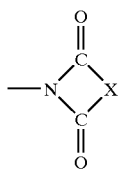

where X is $C_2$–$C_4$ alkylene, or R$_4$ is optionally substituted 1-pyrrolyl; and m and n are each independently 0–2. The compounds are said to be useful for the treatment of restenosis, immune disease, and diabetic complications.

Smith, et al., (*Bioorg. Med. Chem. Lett.* 5:2783–2788 (1995)) reported the anti-rheumatic potential of a series of 2,4-di-substituted-4H-naphtho[1,2-b]pyran-3-carbonitriles. They reported that 4-(3-nitrophenyl)-2-(N-succinimido)-4H-naphtho[1,2-b]pyran-3-carbonitrile has proved to be acid stable and still retains biological activity:

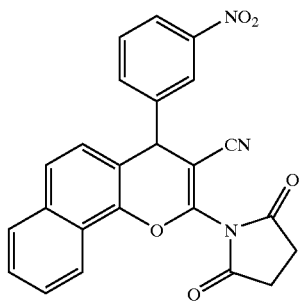

Birch, et al., (*Diabetes* 45:642–650 (1996)) reported that LY290181, an inhibitor of diabetes-induced vascular dysfunction, blocks protein kinase C-stimulated transcriptional activation through inhibition of transcription factor binding to a phorbol response element.

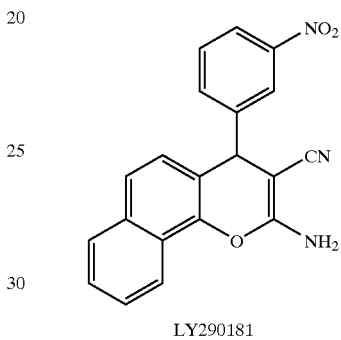

LY290181

Panda, et al., (*J. Biol. Chem.* 272: 7681–7687 (1997)) reported the suppression of microtubule dynamics by LY290181, which might be the potential mechanism for its antiproliferative action.

Wood, et al., (*Mol. Pharmacol.* 52: 437444 (1997)) reported that LY290181 inhibited mitosis and microtubule function through direct tubulin binding.

PCT published patent application WO9824427 disclosed antimicrotubule compositions and methods for treating or preventing inflammatory diseases. LY290181 was listed as an antimicrotubule agent.

SUMMARY OF THE INVENTION

The present invention is related to the discovery that 7,8-fused 4H-chromene and analogs, as represented in Formula I, are activators of the caspase cascade and inducers of apoptosis. Thus, an aspect of the present invention is directed to the use of compounds of Formula I as inducers of apoptosis.

A second aspect of the present invention is to provide a method for treating, preventing or ameliorating neoplasia and cancer by administering a compound of Formula I to a mammal in need of such treatment.

Many of the compounds within the scope of the present invention are novel compounds. Therefore, a third aspect of the present invention is to provide novel compounds of Formula I, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of Formula I in admixture with one or more pharmaceutically acceptable carriers or diluents.

A fifth aspect of the present invention is directed to methods for the preparation of novel compounds of Formula I.

DETAILED DESCRIPTION OF THE INVENTION

The present invention arises out of the discovery that 7,8-fused 4H-chromene and analogs, as represented in Formula I, are potent and highly efficacious activators of the caspase cascade and inducers of apoptosis. Therefore, compounds of Formula I are useful for treating disorders responsive to induction of apoptosis.

Specifically, compounds useful in this aspect of the present invention are represented by Formula I:

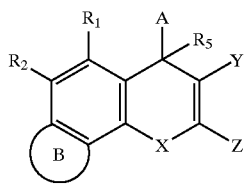

(I)

or pharmaceutically acceptable salts or prodrugs thereof, wherein:

X is O, S or $NR_6$, wherein $R_6$ is hydrogen or optionally substituted alkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_1$–$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic, arylalkyl or heteroarylalkyl; and B is optionally substituted and is a fused thiazole, oxazole, 2-imino-imidazole, 2,1,3-thiadiazo-2-one, thiazol-2-one, oxazol-2-one, imidazol-2-thione, thiazol-2-thione, oxazol-2-thione, imidazoline, oxazoline, thiazoline, triazole, oxazine, oxazine-2,3-dione, or piperazine ring.

Preferred compounds of Formula I include compounds wherein A is phenyl, naphthyl, pyridyl, quinolyl, isoquinolyl, thienyl, furyl, pyrrolyl, 2-phenylethyl or cyclohexyl, any of which is optionally substituted. Other preferred compounds are wherein A is

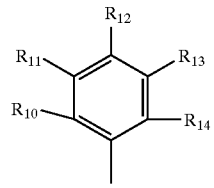

wherein $R_{10}$–$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached, form an aryl, heteroaryl, optionally substituted carbocyclic or optionally substituted heterocyclic group, wherein said group is optionally substituted.

For example, $R_{10}$ and $R_{11}$, or $R_{11}$ and $R_{12}$, may be taken together to form a structure selected from the group consisting of —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, $CH_2N(R)CH_2CH_2$—, —CH=CH—CH=CH—, —N(R)—CH=CH—, —CH=CH—N(R)—, —O—CH=CH—, —CH=CH—O—, —S—CH=CH—, —CH=CH—S—, —N=CH—CH=CH—, —CH=N—CH=CH—, —CH=CH—N=CH—, —CH=CH—CH=N— and —N=CH—CH=N—, wherein R is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

Preferably, $R_5$ is hydrogen. Preferably, X is O or S. Most preferably, X is O. Preferably, Z is $NH_2$. Preferably, Y is CN.

Optional substituents on B include alkyl, cycloalkylalkyl, hydroxyalkyl, epoxyalkyl, alkoxyalkyl, aminoalkyl and haloalkyl. Preferred optional substitutents on B include methyl, hydroxymethyl, cyclopropylmethyl, and 2-N,N-diethylaminoethyl. Preferably, B is N-methyl-oxazol-2-one.

A preferred embodiment is represented by Formula II:

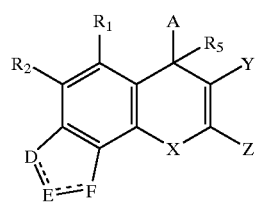

(II)

or pharmaceutically acceptable salts or prodrugs thereof, wherein $R_1$, $R_2$, $R_5$, X, Y, Z and A are as defined previously with respect to Formula I;

D, E, and F are $CR_{15}R_{16}$, C=O, C=S, C=NR is, S=O, N, $NR_{15}$, O, or S, wherein $R_{15}$ and $R_{16}$ are independently hydrogen, alkyl or aryl, provided that the ring comprising D, E and F is not a furan, thiophene, pyrrole, dihydropyrrole, 1,3-dioxolane, cyclopentyl, imidazole or imidazol-2-one ring; and the dashed line represents a single bond or a double bond, with the proviso that both the dashed lines can not be a double bond at the same time.

Such compounds include substituted benzothiazopyrans, benzoxazolepyrans, benzo-(1,2-dihydro-imidazole)pyrans, benzo-(1,2-dihydro-thiazole)pyrans, benzo-(1,2-dihydro-oxazole)pyrans benzo-(1,2-dihydro-2-oxo-imidazole) pyrans, benzo-(1,2-dihydro-2-oxo-thiazole)pyrans, benzo-2-oxo-oxazolepyrans, benzo-(1,2-dihydro-2-thioxo-imidazole)pyrans, benzo-(1,2-dihydro-2-imino-imidazole) pyrans, benzo-(1,3-dihydro-2-oxo-2,1,3-thiadiazole)pyrans, and benzotriazolepyrans.

Preferred compounds falling within the scope of Formula II include compounds wherein $R_1$–$R_2$ are hydrogen. Preferably $R_5$ is hydrogen; X is O; Z is $NH_2$ and Y is CN. Preferably A is optionally substituted phenyl, naphthyl, pyridyl, quinolyl, isoquinolyl, thienyl, furyl, pyrrolyl, 2-phenylethyl or cyclohexyl.

Another preferred embodiment is represented by Formula III:

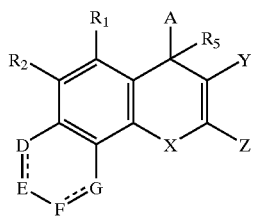

(III)

or pharmaceutically acceptable salts or prodrugs thereof, wherein $R_1$, $R_2$, $R_5$, x, Y, Z and A are as defined previously with respect to Formula I; and D, E, F, and G are $CR_{15}R_{16}$, CO, N, O, or S, wherein $R_{15}$ and $R_{16}$ are defined above, provided that at least two of D, E, F, and G are hetero atoms and the ring comprising D, E, F and G is not a 1,4-dioxolane, pyrazine or 1,4-dihydro-2,3-dioxopyrazine ring; and the dashed lines represent a single bond or a double bond.

Such compounds include substituted benzoxazinepyrans and benzo-2,3-dioxo-oxazinepyrans.

Preferred compounds falling within the scope of Formula III include compounds wherein $R_1$–$R_2$ are hydrogen. Preferably $R_5$ is hydrogen.

Exemplary preferred compounds that may be employed in the method of the invention include, without limitation:

2-Amino-3-cyano-4-(3-bromo-4,5-dimethoxyphenyl)-8-thioxo-4,7,8,9-tetrahydro-imidazo[4,5-h]chromene;

2-Amino-3-cyano-4-(3-methoxyphenyl)-8-thioxo-4,7,8,9-tetrahydro-imidazo[4,5-h]chromene;

2-Amino-3-cyano-4-(3-bromo-4,5-dimethoxyphenyl)-8-imino-4,7,8,9-tetrahydro-imidazo[4,5-h]chromene;

2-Amino-3-cyano-4-(3-methoxyphenyl)-8-imino-4,7,8,9-tetrahydro-imidazo[4,5-h]chromene;

2-Amino-3-cyano-4-(3-bromo-4,5-dimethoxyphenyl)-8-oxo-4,7,9-trihydro-2,1,3-thiadiazo[4,5-h]chromene;

2-Amino-3-cyano-4-(3-methoxyphenyl)-8-oxo-4,7,9-trihydro-2,1,3-thiadiazo[4,5-h]chromene;

2-Amino-3-cyano-4-(3-methoxyphenyl)-8-oxo-4,7,8-trihydro-oxazo[4,5-h]chromene;

2-Amino-3-cyano-4-(3-methoxyphenyl)-4H-oxazo[4,5-h] chromene;

2-Amino-3-cyano-4-(3-methoxyphenyl)-4,7,8,9-tetrahydro-8,9-dioxo-oxazine[2,3-h]chromene;

2-Amino-3-cyano-4-(3-bromo-4,5-dimethoxyphenyl)4,7,8,9-tetrahydro-8,9-dioxo-oxazine[2,3-h]chromene;

2-Amino-3-cyano-4-(3-bromo-4,5-dimethoxyphenyl)-4H-thiazo[4,5-h]chromene;

2-Amino-3-cyano-4-(3-methoxyphenyl)-4H-thiazo[4,5-h] chromene;

2-Amino-3-cyano-4-(3-bromo-4,5-dimethoxyphenyl)-4H-triazo[4,5-h]chromene;

2-Amino-3-cyano-4-(3-methoxyphenyl)-4H-triazo[4,5-h] chromene;

2-Amino-3-cyano 4-(3-bromo-4,5-dimethoxyphenyl)-8-oxo-4,8,9-trihydro-oxazo[5,4-h]chromene;

2-Amino-3-cyano-4-(3-bromo-4,5-dimethoxyphenyl)-8-oxo-4,8-dihydro-9-methyl-oxazo[5,4-h]chromene;

2-Methoxymethylimine-3-cyano-4-(3-bromo-4,5-dimethoxyphenyl)-4H-oxazo[5,4-h]chromene;

2-Amino-3-cyano-4-(3-bromo-4,5-dimethoxyphenyl)-8-oxo-4,7,8-trihydro-oxazo[4,5-h]chromene;

2-Amino-3-cyano-4-(3-bromo-4,5-dimethoxyphenyl)-8-oxo-4,8-dihydro-7-methyl-oxazo[4,5-h]chromene;

2-Amino-3-cyano-4-(3-bromo-4,5-dimethoxyphenyl)-4H-oxazo[4,5-h]chromene; and

2-Amino-3-cyano-4-(3-bromo-4,5-dimethoxyphenyl)-4H-oxazo[5,4-h]chromene.

The present invention is also directed to novel compounds within the scope of Formulae I–III. Exemplary preferred novel compounds of this invention include, without limitation:

2-Amino-3-cyano-4-(3-bromo-4,5-dimethoxyphenyl)-8-thioxo-4,7,8,9-tetrahydro-imidazo[4,5-h]chromene;

2-Amino-3-cyano-4-(3-methoxyphenyl)-8-thioxo-4,7,8,9-tetrahydro-imidazo[4,5-h]chromene;

2-Amino-3-cyano-4-(3-bromo-4,5-dimethoxyphenyl)-8-imino-4,7,8,9-tetrahydro-imidazo[4,5-h]chromene;

2-Amino-3-cyano-4-(3-methoxyphenyl)-8-imino-4,7,8,9-tetrahydro-imidazo[4,5-h]chromene;

2-Amino-3-cyano-4-(3-bromo-4,5-dimethoxyphenyl)-8-oxo-4,7,9-trihydro-2,1,3-thiadiazo[4,5-h]chromene;

2-Amino-3-cyano-4-(3-methoxyphenyl)-8-oxo-4,7,9-trihydro-2,1,3-thiadiazo[4,5-h]chromene;

2-Amino-3-cyano-4-(3-methoxyphenyl)-8-oxo-4,7,8-trihydro-oxazo[4,5-h]chromene;

2-Amino-3-cyano-4-(3-methoxyphenyl)-4H-oxazo[4,5-h] chromene;

2-Amino-3-cyano-4-(3-methoxyphenyl)4,7,8,9-tetrahydro-8,9-dioxo-oxazine[2,3-h]chromene;

2-Amino-3-cyano-4-(3-bromo-4,5-dimethoxyphenyl)4,7,8,9-tetrahydro-8,9-dioxo-oxazine[2,3-h]chromene;

2-Amino-3-cyano-4-(3-bromo-4,5-dimethoxyphenyl)-4H-thiazo[4,5-h]chromene;

2-Amino-3-cyano-4-(3-methoxyphenyl)-4H-thiazo[4,5-h] chromene;

2-Amino-3-cyano-4-(3-bromo-4,5-dimethoxyphenyl)-4H-triazo[4,5-h]chromene;

2-Amino-3-cyano-4-(3-methoxyphenyl)-4H-triazo[4,5-h] chromene;

2-Amino-3-cyano-4-(3-bromo-4,5-dimethoxyphenyl)-8-oxo-4,8,9-trihydro-oxazo[5,4-h]chromene;

2-Amino-3-cyano-4-(3-bromo-4,5-dimethoxyphenyl)-8-oxo-4,8-dihydro-9-methyl-oxazo[5,4-h]chromene;

2-Methoxymethylimine-3-cyano-4-(3-bromo-4,5-dimethoxyphenyl)-4H-oxazo[5,4-h]chromene;

2-Amino-3-cyano-4-(3-bromo-4,5-dimethoxyphenyl)-8-oxo-4,7,8-trihydro-oxazo[4,5-h]chromene;

2-Amino-3-cyano-4-(3-bromo-4,5-dimethoxyphenyl)-8-oxo-4,8-dihydro-7-methyl-oxazo[4,5-h]chromene;

2-Amino-3-cyano-4-(3-bromo-4,5-dimethoxyphenyl)-4H-oxazo[4,5-h]chromene; and

2-Amino-3-cyano-4-(3-bromo-4,5-dimethoxyphenyl)-4H-oxazo[5,4-h]chromene.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which can be optionally substituted.

Useful alkoxy groups include oxygen substituted by one of the $C_{1-10}$ alkyl groups mentioned above, which can be optionally substituted.

Useful alkylthio groups include sulphur substituted by one of the $C_{1-10}$ alkyl groups mentioned above, which can be optionally substituted. Also included are the sulfoxides and sulfones of such alkylthio groups.

Useful amino groups include —$NH_2$, —$NHR_{15}$ and —$NR_{15}R_{16}$, wherein $R_{15}$ is and $R_{16}$ are $C_{1-10}$ alkyl or cycloalkyl groups, or $R_{15}$ and $R_{16}$ are combined with the N to form a ring structure, such as a piperidine, or $R_{15}$ and $R_{16}$ are combined with the N and other group to form a ring, such as a piperazine. The alkyl group can be optionally substituted.

Optional substituents on the alkyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl($C_2$–$C_6$)alkenyl, $C_6$–$C_{10}$ aryl ($C_2$–$C_6$)alkynyl, saturated and unsaturated heterocyclic or heteroaryl. Optional substituents on the aryl, aralkyl and heteroaryl groups include one or more halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

Useful arylalkyl groups include any of the above-mentioned $C_{1-10}$ alkyl groups substituted by any of the above-mentioned $C_{6-14}$ aryl groups. Preferably the arylalkyl group is benzyl, phenethyl or naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, oxazolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido [1,2-a]pyrimidin-4-one, 1,2-benzoisoxazol-3-yl, benzimidazolyl, benzimidazol-2-one, benzoxazolyl, benzoxazol-2-one, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl) aminomethane (TRIS, tromethane) and N-methylglucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (J. Med. Chem. 42:3623–3628 (1999)) and Greenwald, et. al., (J. Med. Chem. 42:3657–3667 (1999)); and acetals and ketals of alcohol containing compounds (e.g., those obtained by condensation with chloromethyl methyl ether or chloromethyl ethyl ether according to methods known in the art); and phosphonato and phosphono compounds (e.g., those obtained by condensation with a phosphate ester, phosphoryl chloride, or phosphoric acid), which include pharmaceutically acceptable mono-basic and di-basic addition salts of the phosphono group, for example, organic bases such as amine bases, which include ammonia, piperidine and morpholine.

The compounds of this invention may be prepared using methods known to those skilled in the art, or the novel methods of this invention. In particular, the compounds of this invention with Formulae I–III can be prepared as illustrated by exemplary reaction in Scheme 1. Reaction of a 2,3-disubstituted phenol, such as 2,3-diaminophenol with a substituted benzaldehyde, such as 3-methoxybenzaldehyde and malononitrile in the presence a base, such as piperidine or N,N-diisopropylethylamine produced the 7,8-diamino chromene, which can then cyclize under different conditions to produce the 7,8-fused chromenes. For example, reaction of the 7,8-diamino chromene with 1,1'-carbonyldiimidazole (CDI) will produce the 2-oxo-imidazole-chromene compound.
Scheme 1
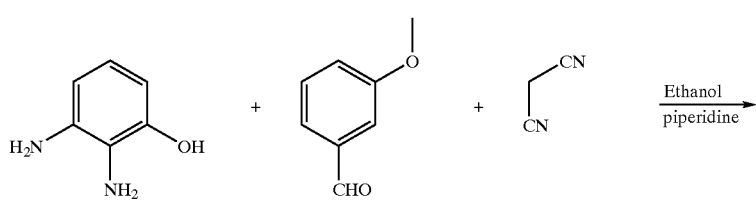

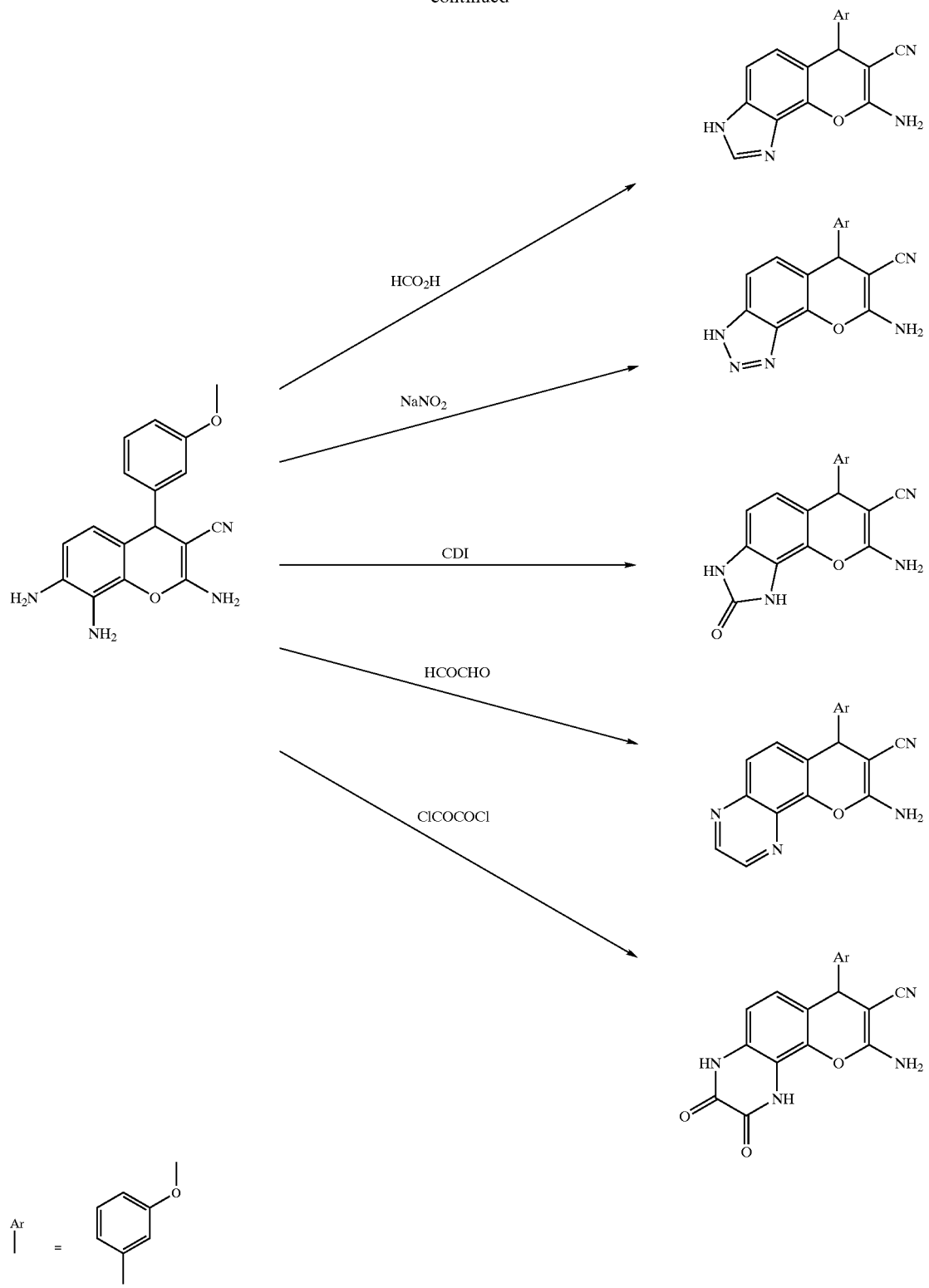

Compounds of this invention with Formulae I–III can be prepared as illustrated by exemplary reaction in Scheme 2. Reaction of the diamino-chromene with $CS_2$ in the presence of a base such as KOH produces the 2-thioxo-imidazo-chromene compound. Reaction of the diamino-chromene with cyanogen bromide (BrCN) produces the 2-imino-imidazo-chromene compound. Reaction of the diamino-chromene with $SOCl_2$ in the presence of a base, such as pyridine produces the 2-oxo-thiadiazo-chromene compound.

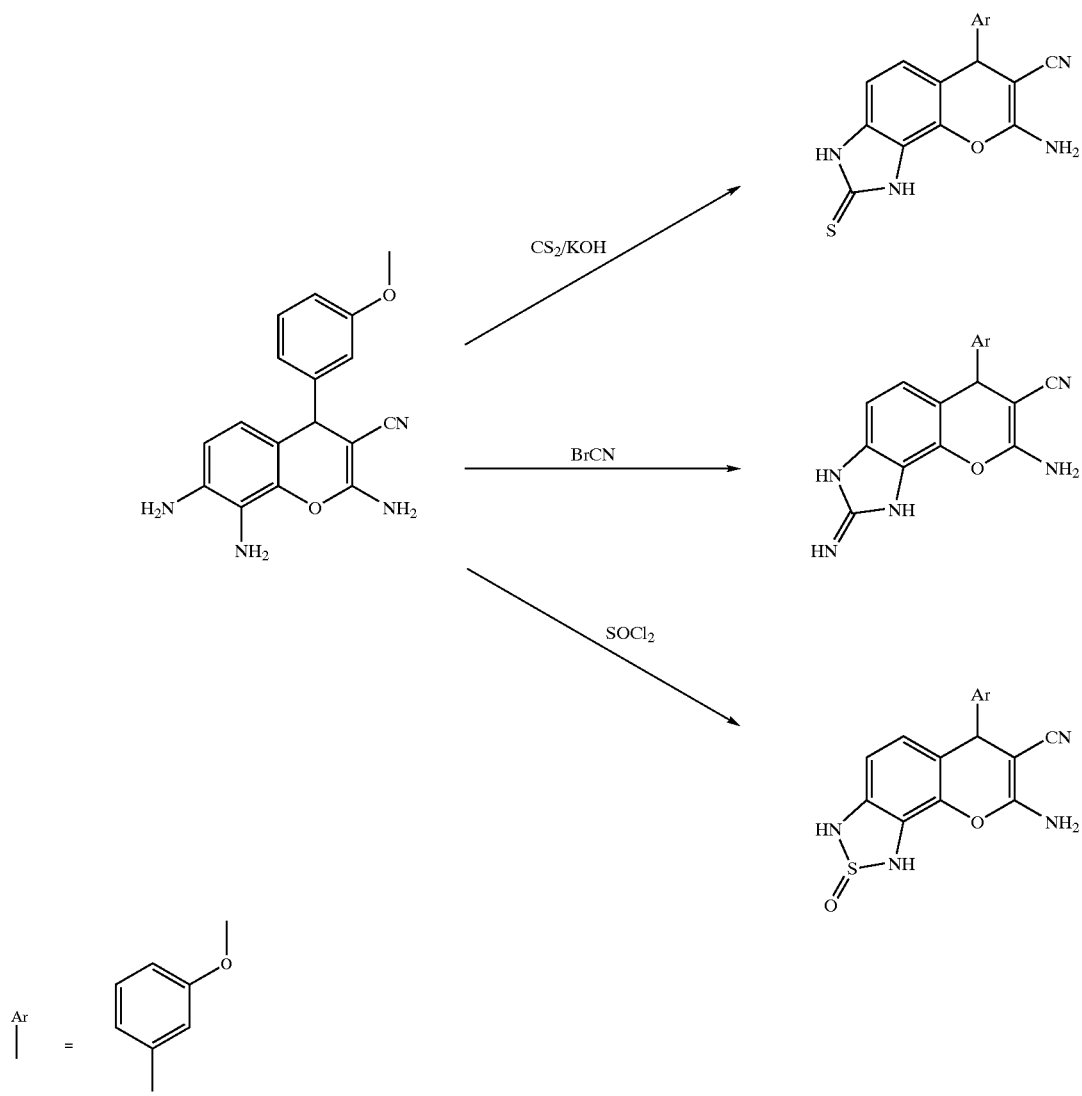

Compounds of this invention with Formulae I–III also can be prepared as illustrated by exemplary reaction in Scheme 3. Reaction of 3-amino-pyrocatechol with a substituted benzaldehyde such as 3-methoxybenzaldehyde and malononitrile in the presence a base such as piperidine or N,N-diisopropylethylamine produces the 7-amino-8-hydroxy chromene, which can then cyclized under different conditions to produce the 7,8-fused chromenes. For example, reaction of the 7-amino-8-hydroxy chromene with 1,1'-carbonyldiimidazole (CDI) produces the 2-oxo-oxazole-chromene compound. Reaction of the 7-amino-8-hydroxy chromene with oxalyl chloride produces the 2,3-dioxo-oxazine-chromene compound.

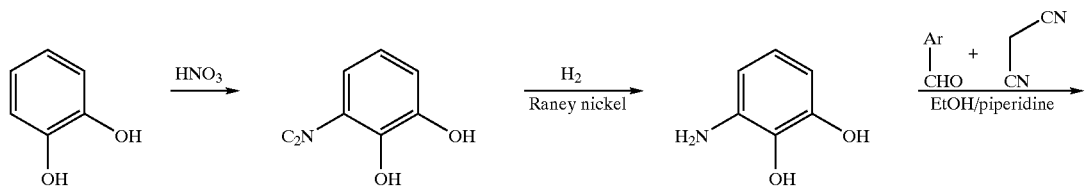

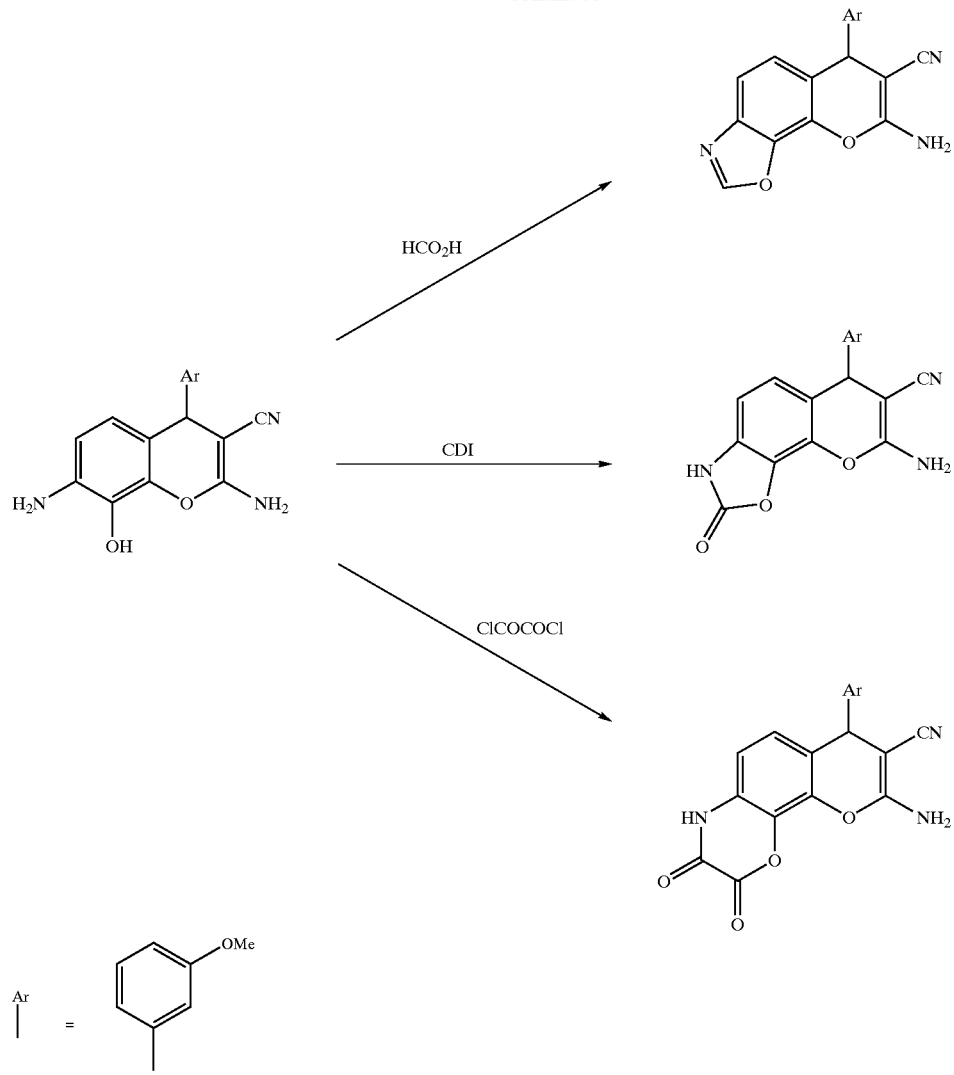

An important aspect of the present invention is the discovery that compounds having Formulae I–III are activators of caspases and inducers of apoptosis. Therefore, these compounds are expected to be useful in a variety of clinical conditions in which there is uncontrolled cell growth and spread of abnormal cells, such as in the case of cancer.

Another important aspect of the present invention is the discovery that compounds having Formulae I–III are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are expected to be useful for the treatment of drug resistant cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I–III, which functions as a caspase cascade activator and inducer of apoptosis.

The present invention also include a therapeutic method comprising administering to an animal an effective amount of a compound, or a pharmaceutically acceptable salt or prodrug of said compound of Formulae I–III, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms In another embodiment, a pharmaceutical composition comprising a compound, or a pharmaceutically acceptable salt of said compound of Formulae I–III, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I-III, which functions as a caspase cascade activator and inducer of apoptosis, in combination with at least one known cancer chemotherapeutic agent, or a pharmaceutically acceptable salt of said agent. Examples of known anti-cancer agents, which can be used for combination therapy include, but not are limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from the at least one known cancer chemotherapeutic agent. In one embodiment, the compound of the invention and the at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I–III, which functions as a caspase cascade activator and inducer of apoptosis, in bioconjugation with at least one known therapeutically useful antibodies, such as Herceptin® or Rituxan®; growth factors, such as DGF, NGF; cytokines, such as IL-2, IL-4; or any molecule that binds to cell surface. The antibodies and other molecules will deliver compound of Formulae I–III to its targets and make them effective anticancer agents. The bioconjugates also could enhance the anticancer effect of therapeutically useful antibodies, such as Herceptin® or Rituxan®.

Similarly, another embodiment of the present invention is directed to a composition effective to inhibit neoplasia comprising a compound or a pharmaceutically acceptable salt or prodrug of said compound of Formulae I–III, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–III, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629–633 (1998) and Vaishnaw, A. K., et al., *J. Clin. Invest.* 103:355–363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475–483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:4248 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I–III, which functions as a caspase cascade activator and inducer of apoptosis, should be an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al., *Photodermatol Photoimmunol. Photomed.* 15:22–27 (1999), reported that lymphocytes treated with psoralen 8-MOP or TMP plus UVA displayed DNA degradation patterns typical of apoptotic cell death. Ozawa, et al., *J. Exp. Med.* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and this mode of action could explain the reduction in epidermal hyperplasia during treatment of psoriasis with methotrexate. Therefore, an effective amount of a compound, or a pharmaceutically acceptable salt or prodrug of the compound of Formulae I–III, which functions as a caspase cascade activator and inducer of apoptosis, should be an effective treatment for hyperproliferative skin diseases, such as psoriasis.

Synovial cell hyperplasia is a characteristic of patients with rheumatoid arthritis (RA). Excessive proliferation of RA synovial cells, as well as defective in synovial cell death, might be responsible for the synovial cell hyperplasia Wakisaka, et al., *Clin. Exp. Immunol.* 114:119–128 (1998), found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I–III, which functions as a caspase cascade activator and inducer of apoptosis, should be an effective treatment for rheumatoid arthritis.

There have been accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375–380 (1997)). Boirivant, et al., *Gastroenterology* 116:557–565 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I–III, which functions as a caspase cascade activator and inducer of apoptosis, should be an effective treatment for inflammation and inflammatory bowel disease.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day, of the body weight of the mammal being treated for apoptosis-mediated disorders. Preferably, approximately 0.01 to approximately 10 mg/kg is orally administered to treat or prevent such disorders. For intramuscular injection, the dose is generally approximately one-half of the oral dose. For example, a suitable intramuscular dose would be approximately 0.0025 to approximately 25 mg/kg, and most preferably, from approximately 0.01 to approximately 5 mg/kg. If a known cancer chemotherapeutic agent is also administered, it is administered in an amount with is effective to achieve its intended purpose. The amounts of such known cancer chemotherapeutic agents effective for cancer are well known to those of skill in the art.

The unit oral dose may be comprised of approximately 0.01 to approximately 50 mg, preferably approximately 0.1 to approximately 10 mg of the compound of the invention. The unit dose may be administered one or more times daily as one or more tablets, each containing from approximately 0.1 to approximately 10, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from approximately 0.01 to 99 percent, preferably from approximately 0.25 to 75 percent of active compound (s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base, such as sodium hydroxide, potassium hydroxide, choline hydroxide, sodium carbonate, Tris, N-methyl-glucamine, and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Administration, alternatively, or concurrently, may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers, such as saccharides, e.g., lactose or sucrose, mannitol or sorbitol; cellulose preparations and/or calcium phosphates, e.g., tricalcium phosphate or calcium hydrogen phosphate, as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose; binders, such as starches, and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400) cremophor, or cyclodextrins. Aqueous injection suspensions may contain substances, which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil with warm soft paraffin and allowing the mixture to cool. A typical example of such an ointment is one which includes approximately 30% almond oil and approximately 70% white soft paraffin by weight.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

EXAMPLE 1

2-Amino-3-cyano-4-(3-bromo-4,5-dimethoxyphenyl)-4H-triazo[4,5-h]chromene

In a round bottle (20 mL) was placed 2,7,8-triamino-3-cyano-4-(3-bromo-4,5-dimethoxyphenyl)-4H-chromene (320 mg, 0.8 mmol), glacial acetic acid (1.0 mL, 1.6 mmol) and water (1 mL). The mixture was slightly warmed and a clear solution was obtained. The bottle was placed in ice water and the contents cooled to approximately 5° C., and a cold solution of sodium nitrite (55 mg, 0.8 mmol) in 0.5 mL $H_2O$ was added. The mixture was stirred for approximately 3 h at room temperature and the color darkened. The mixture was extracted using ethyl acetate and the extract was evaporated. The residue was purified by column chromatography (silica gel, hexane:EtOAc, 2:1) to yield 147 mg (43%) of the title compound. $^1$H NMR ($CD_3OD$): 7.76 (d, J=5.5, 1H), 7.16 (d, J=2.4 Hz, 1H), 7.11 (d, J=5.5 Hz, 1H), 7.03 (d, J=2.4 Hz, 1H), 4.59 (s, 1H), 3.91 (s, 3H), 3.84 (s, 3H).

EXAMPLE 2

2-Amino-3-cyano-4-(3-bromo-4,5-dimethoxyphenyl)-8-oxo-4,8,9-trihydro-oxazo[5,4-h]chromene 1,1'-Carbonyldiimidazole (17.1 mg, 0.11 mmol, 1.5 eq.) was added to a solution of 2-amino-3-cyano-7-hydroxy-8-amino-4-(3-bromo-4,5-dimethoxyphenyl)-4H-chromene (29.4 mg, 0.07 mmol) in toluene (1 mL). The reaction mixture was heated to approximately 60° C. and stirred for approximately 18 h. The solvent was evaporated and the crude solid was washed with methanol several times to remove the soluble imidazole. The desired compound was dried under vacuum to yield 14.7 mg of a white solid. $^1$H NMR ($CDCl_3$): 7.03–6.98 (m, 2H), 6.91–6.86 (m, 1H), 6.81 (s, 2H), 6.78 (d, J=0.7 Hz, 1H), 4.79 (s, 1H), 3.79 (s, 3H), 3.68 (s, 3H).

EXAMPLE 3

2-Amino-3-cyano-4-(3-bromo-4,5-dimethoxyphenyl)-8-oxo-4,8-dihydro-9-methyl-oxazo[5,4-h]chromene Cesium carbonate (14 mg, 0.04 mmol, 1 eq.) was added to a solution of 2-amino-3-cyano-4-(3-bromo-4,5-dimethoxyphenyl)-8-oxo-4,8,9-trihydro-oxazo[5,4-h]chromene (19.7 mg, 0.04 mmol) in dimethylformamide (2 mL), followed by a solution of iodomethane (2M in t-butyl methyl ether) (22 μL, 0.04 mmol, 1 eq.). The reaction mixture was stirred at room temperature overnight. The solvent was evaporated and the crude material was purified by Biotage flash chromatography (cartridge 12S, $SiO_2$) (Dyax Corporation) using approximately 0% to 2% methanol in dichloromethane to yield 9.5 mg of the desired compound. $^1$H NMR ($CD_3OD$): 7.00 (d, J=8.4 Hz, 1H), 6.95 (d, J=2.0 Hz, 1H), 6.91 (d, J=2.0 Hz, 1H), 6.84 (m, 1H), 4.76 (s, 1H), 3.86 (s, 3H), 3.79 (s, 3H), 3.68 (s, 3H).

EXAMPLE 4

2-Methoxymethylimine-3-cyano-4-(3-bromo-4,5-dimethoxyphenyl)-4H-oxazo[5,4-h]chromene p-Toluenesulfonic acid (3 mg) was added to a solution of 2-amino-3-cyano-7-hydroxy-8-amino-4-(3-bromo-4,5-dimethoxyphenyl)-4H-chromene (25.2 mg, 0.06 mmol) in toluene (1 mL) followed by methylorthoformate (1 mL). The reaction mixture was heated to approximately 50° C. and stirred for approximately 1 h. The mixture was poured into saturated aqueous sodium bicarbonate solution (10 mL). The aqueous layer was extracted with ethyl acetate (3×10 mL). The organic layers were combined, dried over sodium sulfate, filtered and concentrated. The crude product was purified by Biotage flash chromatography (cartridge 12S, $SiO_2$) using approximately 35% ethyl acetate in hexane to yield 15.5 mg of the desired compound. $^1$H NMR ($CDCl_3$): 8.59 (s, 1H), 8.07 (s, 1H), 7.27 (d, J=8.5 Hz, 1H), 6.95 (d, J=8.6 Hz, 1H), 6.84 (d, J=2.1 Hz, 1H), 6.70 (d, J=2.1 Hz, 1H), 4.85 (s, 1H), 3.93 (d, J=0.7 Hz, 1H), 3.77 (s, 3H), 3.77 (s, 3H)

EXAMPLE 5

2-Amino-3-cyano-4-(3-bromo-4,5-dimethoxyphenyl)-8-oxo-4,7,8-trihydro-oxazo[4,5-h]chromene (a) 2,3-Dihydroxybenzoic acid: 2,3-Dimethoxybenzoic acid (2 g, 10.98 mmol) was dissolved in acetic acid (25 mL). Hydriodic acid (approximately 47% solution in water) (25 mL) was added and the reaction mixture was heated under reflux overnight. The reaction was allowed to cool to room temperature and the solvent removed under vacuum. The yellow solid was dissolved in a minimum of water and extracted with ethyl acetate (4×50 mL). The organic layers were combined, washed with approximately 10% sodium thiosulfate solution (2×50 mL), water (50 mL) and brine (50 mL). The organic layer was dried over sodium sulfate, filtered and concentrated under vacuum to yield 1.68 g (99%) of 2,3-dihydroxybenzoic acid as a white solid. $^1$H NMR ($CD_3OD$): 7.34 (d, J=8.0 Hz, 1H), 6.99 (d, J=8.0 Hz, 1H), 6.72 (t, J=8.0 Hz, 1H).

(b) 7-Hydroxy-3H-benzooxazol-2-one: Diphenylphosphorylazide (336 μL, 1.56 mmol, 1.2 eq) was added to 2,3-dihydroxybenzoic acid (200 mg, 1.30 mmol) in pyridine (10 mL) and heated at approximately 75° C. for approximately 30 h. The reaction mixture was allowed to cool to room temperature and the reaction was quenched with water. Pyridine was removed under vacuum and the residue was partitioned between ethyl acetate (20 mL) and a solution of saturated aqueous sodium bicarbonate:water (1:1, 20 mL). The aqueous layer was extracted with ethyl acetate (3×20 mL). The organic layers were combined, washed with brine, dried over sodium sulfate, filtered and concentrated under vacuum to yield a yellow oil. The desired product was isolated by Biotage flash chromatography (cartridge 40S, $SiO_2$) using approximately 0%, 15%, 25% and 50% ethyl acetate in hexanes as eluant to yield 104 mg (53%) of 7-hydroxy-3H-benzooxazol-2-one as a white powder. $^1$H NMR ($CD_3OD$): 6.96 (dd, J=8.4, 7.8 Hz, 1H), 6.59 (d, J=8.4 Hz, 1H), 6.56 (d, J=7.8 Hz, 1H).

(c) 2-Amino-3-cyano-4-(3-bromo-4,5-dimethoxyphenyl)-8-oxo-4,7,8-trihydro-oxazo[4,5-h]chromene: 7-Hydroxy-3H-benzooxazol-2-one (300 mg, 1.98 mmol), 5-bromoveratraldehyde (486 mg, 1.98 mmol) and malononitrile (131 mg, 1.98 mmol) were dissolved in ethanol (12 mL). Piperidine (390 μL, 3.96 mmol) was added and the reaction stirred at room temperature overnight. The precipitate was filtered and dried to yield 338.5 mg (38%) of the desired 2-amino-3-cyano-4-(3-bromo-4,5-dimethoxyphenyl)-8-oxo-4,7,8-trihydrooxazo[4,5-h]chromene as a light yellow powder. $^1$H NMR (DMSO-$d_6$) 11.79 (s, 1H), 7.21 (brs, 2H), 6.98 (s, 1H), 6.91 (s, 1H), 6.85–6.79 (m, 2H), 4.79 (s, 1H), 3.78 (s, 3H), 3.68 (s, 3H).

EXAMPLE 6

2-Amino-3-cyano-4-(3-bromo-4,5-dimethoxyphenyl)-8-oxo-4,8-dihydro-7-methyl-oxazo[4,5-h]chromene 2-amino-3-cyano-4-(3-bromo-4,5-dimethoxyphenyl)-8-oxo-4,7,8-trihydro-oxazo[4,5-h]chromene (335 mg, 0.75 mmol) and cesium carbonate (270 mg, 0.83 mmol) were dissolved in anhydrous acetone (10 mL). Methyl iodide (2M solution in t-BuOMe, 415 μL, 0.83 mmol) was added and the reaction stirred at room temperature overnight. The solvent was removed under vacuum and the residue partitioned between water (20 mL) and ethyl acetate (60 mL). The aqueous layer was extracted with ethyl acetate (2×50 mL). The organic layers were combined, dried over sodium sulfate, filtered and concentrated to a yellow solid. The product was isolated by Biotage flash chromatography (cartridge 25S, $SiO_2$) using 0 to 1% methanol in dichloromethane to yield 292 mg (85%) of the title compound as a light yellow solid. $^1$H NMR (Acetone-$d_6$): 7.04–6.93 (m, 4H), 6.49 (brs, 2H), 4.83 (s, 1H), 3.86 (s, 3H), 3.76 (s, 3H), 3.39 (s, 3H).

EXAMPLE 7

2-Amino-3-cyano-4-(3-bromo-4,5-dimethoxyphenyl)-4H-oxazo[4,5-h]chromene (a) 2,3-dihydroxyaniline: 2,3-dimethoxyaniline (500 mg, 3.26 mmol) was dissolved in acetic acid (10 mL). Hydriodic acid (approximately a 47% solution in water) (10 mL) was added and the reaction was heated under reflux for approximately 8 h. The reaction was cooled to room temperature and stirred for approximately 3 days. The solvent was removed under vacuum and the yellow solid dissolved in water and neutralized with saturated aqueous sodium bicarbonate solution. The aqueous layer was extracted with ethyl acetate (4×20 mL). The organic layers were combined, washed with a solution of approximately 10% aqueous sodium thiosulfate (30 mL), water (30 mL) brine (30 mL), dried over sodium sulfate, filtered and concentrated. The crude product was purified by Biotage (cartridge 40S, $SiO_2$) using approximately a 1%, 2% and 4% methanol solution in dichloromethane to yield 188 mg (46%) of 2,3-dihydroxyaniline as a beige solid. $^1$H NMR ($CD_3OD$): 6.47 (t, J=8.0 Hz, 1H), 6.28 (dd, J=8.0, 1.6 Hz, 1H), 6.24 (dd, J=8.0, 1.6 Hz, 1H).

(b) 2-Amino-3-cyano-7-amino-8-hydroxy-4-(3-bromo-4,5-dimethoxyphenyl)-4H-chromene: 2,3-dihydroxyaniline (80 mg, 0.64 mmol), 5-bromoveratraldehyde (157 mg, 0.64 mmol) and malononitrile (42 mg, 0.64 mmol) were dissolved in ethanol (4 mL). Piperidine (127 μL, 1.28 mmol) was added and the reaction stirred at room temperature overnight. The reaction mixture was concentrated under vacuum and the desired product isolated by Biotage flash chromatography (cartridge 12M) with approximately 2% and 5% methanol solutions in dichloromethane as eluant to yield 97 mg (36%) of the desired product as a brown foamy solid. $^1$H NMR ($CD_3OD$): 6.86 (s, 1H), 6.80 (s, 1H), 6.47 (d, J=8.0 Hz, 1H), 6.29 (d, J=8.0 Hz, 1H), 4.56 (s, 1H), 3.78 (s, 3H), 3.75 (s, 3H).

(c) 2-Amino-3-cyano-4-(3-bromo-4,5-dimethoxyphenyl)-4H-oxazo[4,5-h]chromene: 2-amino-3-cyano-7-amino-8-hydroxy-4-(3-bromo-4,5-dimethoxyphenyl)-4H-chromene (30 mg, 0.07 mmol) was dissolved in toluene (1 mL) and THF (1 mL). Trimethylorthoformate (24 μL, 0.22 mmol, 3 eq), and p-toluenesulfonic acid (2.7 mg, 0.01 mmol, 0.2 eq) were added and the reaction stirred at approximately 50° C. overnight. The reaction mixture was allowed to cool to room temperature and quenched with saturated aqueous sodium bicarbonate solution (10 mL). The aqueous layer was extracted with ethyl acetate (3×20 mL). The organic layers were combined, dried over sodium sulfate, filtered and concentrated to yield a brown oil. The product was isolated by Biotage flash chromatography (cartridge 12S, $SiO_2$) using approximately 0%, 2% and 4% methanol solutions in dichloromethane as eluant to yield 13.5 mg of a yellow oily solid. NMR showed impurities in the aliphatic region. The product was re-crystallized in a minimum of methanol. The crystals were washed with diethyl ether to yield 4.6 mg (15%) of the title compound as a yellow solid. $^1$H NMR (DMSO-$d_6$): 8.79 (s, 1H), 7.49 (d, J=8.0 Hz, 1H), 7.28 (brs, 2H), 7.09 (d, J=8.0 Hz, 1H), 7.02 (s, 1H), 6.95 (s, 1H), 4.93 (s, 1H), 3.79 (s, 3H), 3.68 (s, 3H).

EXAMPLE 8

2-Amino-3-cyano-4-(3-bromo-4,5-dimethoxyphenyl)-4H-oxazo[5,4-h]chromene

A similar procedure as Example 7c was used to prepare the title compound: $^1$H NMR (acetone-$d_6$): 8.52 (d, J=0.3 Hz, 1), 7.42 (d, J=8.5 Hz, 1H), 7.22–7.19 (m, 1H), 7.07–7.04 (m, 2H), 6.51 (brs, 2H), 4.93 (s, 1H), 3.85 (s, 3H), 3.76 (s, 3H).

EXAMPLE 9

Identification of Compounds as Caspase Cascade Activators and Inducers of Apoptosis in Solid Tumor Cells Human breast cancer cell lines T47D and ZR-75-1 were grown according to media component mixtures designated by American Type Culture Collection+10% FCS (Invitrogen Corporation), in approximately 5% $CO_2$-95% humidity incubator at approximately 37° C. T-47D and ZR-75–1 cells were maintained at a cell density between 30 and 80% confluency at a cell density of 0.1 to 0.6×10$^6$ cells/mL. Cells were harvested at approximately 600×g and resuspended at approximately 0.65×10$^6$ cells/mL into appropriate media plus approximately 10% FCS. An aliquot of approximately 45 μl of cells was added to a well of a 96-well microtiter plate containing approximately 5 μl of a solution of approximately 10% DMSO in RPMI-1640 media solution containing approximately 0.16 to 10 μM of the test compounds (0.016 to 1 μM final). An aliquot of approximately 45 μl of cells was added to a well of a 96-well microtiter plate containing approximately 5 μl of a solution of approximately 10% DMSO in RPMI-1640 media solution without test compound as the control sample. The samples were mixed by agitation and then incubated at approximately 37° C. for approximately 24 h in approximately 5% $CO_2$-95% humidity incubator. After incubation, the samples were removed from the incubator and approximately 50 μl of a solution containing approximately 20 μM of N-(Ac-DEVD)-N'-ethoxycarbonyl-R110 fluorogenic substrate, SEQ ID NO:1 (Cytovia, Inc.; U.S. Pat. No. 6,335,429), comprising approximately 20% sucrose (Sigma), 20 mM DTT (Sigma), 200 mM NaCl (Sigma), 40 mM Na PIPES buffer at approximate pH 7.2 (Sigma), and approximately 500 μg/ml lysolecithin (Calbiochem) was added. The samples were mixed by agitation and incubated at room temperature. Using a fluorescent plate reader (Model 1420 Wallac Instruments), an initial reading (T=0) was made approximately 1–2 min after addition of the substrate solution, employing excitation at 485 nm and emission at 530 mm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for the test compounds to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

CASPASE ACTIVITY AND POTENCY

| Example # | T-47D Ratio | T-47D EC50 (nM) | ZR-75-1 Ratio | ZR-75-1 EC50 (nM) |
|---|---|---|---|---|
| 1 | 1.8 | >1000 | 5.3 | 560 |
| 2 | 6.4 | 566.6 | 8.5 | 365.6 |
| 3 | 1.5 | Inactive | 2.7 | 2501.3 |
| 4 | 8.1 | 47.2 | 7.9 | 23.0 |
| 5 | 8.6 | 284.7 | 4.5 | 156.2 |
| 6 | 6.5 | 11.8 | | |
| 7 | 7.8 | 68.7 | 9.8 | 43.0 |
| 8 | 7.9 | 35.1 | 7.2 | 12.9 |

Thus, these compounds are identified as potent caspase cascade activators and inducers of apoptosis in solid tumor cells.

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Fluorogenic substrate

<400> SEQUENCE: 1

Asp Glu Val Asp
1

What is clamed is:

1. A compound of Formula I:

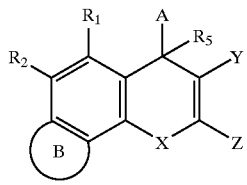

(I)

or a pharmaceutically acceptable salt or prodrug thereof, wherein:

X is O, S or $NR_6$, wherein $R_6$ is hydrogen or optionally substituted alkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_1$–$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl; and B is optionally substituted and is a fused thiazole, oxazole, 2-imino-imidazole, 2,1,3-thiadiazo-2-one, thiazol-2-one, oxazol-2-one, oxazol-2-thione, imidazol-2-thione, thiazol-2-thione, imidazoline, oxazoline, thiazoline, triazole, oxazine, oxazine-2,3-dione, or piperazine ring.

2. The compound of claim 1, wherein B is N-methyloxazol-2-one.

3. A compound of Formula II:

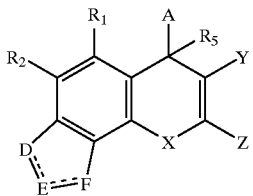

(II)

or pharmaceutically acceptable salts or prodrugs thereof, wherein

X is O, S or $NR_6$, wherein $R_6$ is hydrogen or optionally substituted alkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to form a heterocycle;

Z is $NR_8R_9$, $NHCOR_8$, $N(COR_8)_2$, $N(COR_8)(COR_9)$, N=$CHOR_8$ or N=$CHR_8$, wherein $R_8$ and $R_9$ are independently H, $C_{1-4}$ alkyl or aryl, or $R_8$ and $R_9$ are combined together with the group attached to them to form a heterocycle;

$R_1$–$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl;

D, E and F are $CR_{15}R_{16}$, CO, N, O, or S, wherein $R_{15}$ and $R_{16}$ are independently hydrogen or alkyl; provided that at least two of D, E and F are hetero atoms, at least one of D, E and F is N, and the ring comprising D, E and F is not a imidazol-2-one or imidazole ring; and the dashed line represents a single bond or a double bond, with the proviso that both the dashed lines can not be a double bond at the same time.

4. The compound of claim 3, wherein the ring comprising D, E and F is N-methyloxazol-2-one.

5. The compound of claim 3, wherein said compound is 2-Amino-3-cyano-4-(3-bromo-4,5-dimethoxyphenyl)-8-thioxo-4,7,8,9-tetrahydro-imidazo[4,5-h]chromene;
2-Amino-3-cyano-4-(3-methoxyphenyl)-8-thioxo-4,7,8,9-tetrahydro-imidazo[4,5-h]chromene;
2-Amino-3-cyano-4-(3-bromo-4,5-dimethoxyphenyl)-8-imino-4,7,8,9-tetrahydro-imidazo[4,5-h]chromene;
2-Amino-3-cyano-4-(3-methoxyphenyl)-8-imino-4,7,8,9-tetrahydro-imidazo[4,5-h]chromene;
2-Amino-3-cyano-4-(3-bromo-4,5-dimethoxyphenyl)-8-oxo-4,7,9-trihydro-2,1,3-thiadiazo[4,5-h]chromene;
2-Amino-3-cyano-4-(3-methoxyphenyl)-8-oxo-4,7,9-trihydro-2,1,3-thiadiazo[4,5-h]chromene;
2-Amino-3-cyano-4-(3-methoxyphenyl)-8-oxo-4,7,8-trihydro-oxazo[4,5-h]chromene;
2-Amino-3-cyano-4-(3-methoxyphenyl)-4H-oxazo[4,5-h]chromene;
2-Amino-3-cyano-4-(3-bromo-4,5-dimethoxyphenyl)-4H-thiazo[4,5-h]chromene;
2-Amino-3-cyano-4-(3-methoxyphenyl)-4H-thiazo[4,5-h]chromene;
2-Amino-3-cyano-4-(3-bromo-4,5-dimethoxyphenyl)-4H-triazo[4,5-h]chromene;
2-Amino-3-cyano-4-(3-methoxyphenyl)-4H-triazo[4,5-h]chromene;
2-Amino-3-cyano-4-(3-bromo-4,5-dimethoxyphenyl)-8-oxo-4,8,9-trihydro-oxazo[5,4-h]chromene;
2-Amino-3-cyano-4-(3-bromo-4,5-dimethoxyphenyl)-8-oxo-4,8-dihydro-9-methyl-oxazo[5,4-h]chromene;
2-Methoxymethylimine-3-cyano-4-(3-bromo-4,5-dimethoxyphenyl)-4H-oxazo[5,4-h]chromene;
2-Amino-3-cyano-4-(3-bromo-4,5-dimethoxyphenyl)-8-oxo-4,7,8-trihydro-oxazo[4,5-h]chromene;
2-Amino-3-cyano-4-(3-bromo-4,5-dimethoxyphenyl)-8-oxo-4,8-diihydro-7-methyl-oxazo[4,5-h]chromene;
2-Amino-3-cyano-4-(3-bromo-4,5-dimethoxyphenyl)-4H-oxazo[4,5-h]chromene; and
2-Amino-3-cyano-4-(3-bromo-4,5-dimethoxyphenyl)-4H-oxazo[5,4-h]chromene.

6. A compound which has the Formula III:

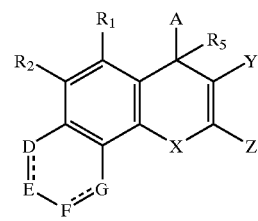

(III)

or pharmaceutically acceptable salts or prodrugs thereof, wherein

X is O, S or $NR_6$, wherein $R_6$ is hydrogen or optionally substituted alkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to form a heterocycle;

Z is $NR_8R_9$, $NHCOR_8$, $N(COR_8)_2$, $N(COR_8)(COR_9)$, N=$CHOR_8$ or N=$CHR_8$, wherein $R_8$ and $R_9$ are independently H, $C_{1-4}$ alkyl or aryl, or $R_8$ and $R_9$ are combined together with the group attached to them to form a heterocycle;

$R_1$–$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl;

D, E, F, and G are $CR_{15}R_{16}$, CO, N, O, or S, wherein $CR_{15}$ and $R_{16}$ are independently hydrogen or alkyl, provided that at least two of D, E, F, and G are hetero atoms, at least one of D, E, F and G is N, and the ring comprising D, E, F and G is not a 1,4-dihydro-2,3-dioxopyrazine or pyrazine ring; and the dashed lines represent a single bond or a double bond.

7. The compound of claim 6, wherein said compound is 2-Amino-3-cyano-4-(3-methoxyphenyl)-4,7,8,9-tetrahydro-8,9-dioxo-oxazine[2,3-h]chromene; and 2-Amino-3-cyano-4-(3-bromo-4,5-dimethoxyphenyl)-4,7,8,9-tetrahydro-8,9-dioxo-oxazine[2,3-h]chromene.

8. A pharmaceutical composition, comprising the compound of any one of claims 1–7 and a pharmaceutically acceptable excipient or carrier.

9. The pharmaceutical composition of claim 8, further comprising at least one known cancer chemotherapeutic agent, or a pharmaceutically acceptable salt of said agent.

10. The pharmaceutical composition of claim 9, wherein said known cancer chemotherapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin®, Rituxan® and alanosine.

11. The pharmaceutical composition of claim 8, wherein said excipient or carrier is selected from the group consisting of saccharides, starch pastes, gelatin, tragacanth, cellulose preparations, calcium phosphates and polyvinyl pyrrolidone.

12. A method of treating a disorder responsive to the induction of apoptosis in an animal suffering therefrom, comprising administering to a mammal in need of such treatment, an effective amount of a compound of claim 1.

13. The method of claim 12, wherein B is N-methyloxazol-2-one.

14. The method of claim 12, wherein X is O.

15. The method of claim 12, wherein A is optionally substituted and selected from the group consisting of phenyl, naphthyl, quinolyl, isoquinolyl, pyridyl, thienyl, furyl, pyrrolyl, 2-phenylethyl and cyclohexyl.

16. The method of claim 12, wherein X is O, Y is CN and Z is $NH_2$.

17. The method of claim 12, wherein $R_5$ is hydrogen.

18. The method of claim 12, wherein A is

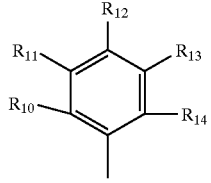

and $R_{10}$–$R_{14}$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_{10}$ and $R_{11}$, or $R_{11}$ and $R_{12}$, taken together with the atoms to which they are attached form an aryl, heteroaryl, optionally substituted carbocyclic or optionally substituted heterocyclic group, wherein said group is optionally substituted.

19. The method of claim 18, wherein $R_{10}$ and $R_{11}$, or $R_{11}$ and $R_{12}$, are taken together to form a structure selected from the group consisting of —$OCH_2O$—, —$(CH_2)_3$—, —$(CH_2)_4$—, —$OCH_2CH_2O$—, —$CH_2N(R)CH_2$—, —$CH_2CH_2N(R)CH_2$—, —$CH_2N(R)CH_2CH_2$—, —CH=CH—CH=CH—, —N(R)—CH=CH—, —CH=CH—N(R)—, —O—CH=CH—, —CH=CH—O—, —S—CH=CH—, —CH=CH—S—, —N=CH—CH=CH—, —CH=N—CH=CH—, —CH=CH—N=CH—, —CH=CH—CH=N— and —N=CH—CH=N—, wherein R is hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

20. The method of claim 19, wherein said compound is 2-Amino-3-cyano-4-(3-bromo-4,5-dimethoxyphenyl)-8-thioxo-4,7,8,9-tetrahydro-imidazo[4,5-h]chromene;

2-Amino-3-cyano-4-(3-methoxyphenyl)-8-thioxo-4,7,8,9-tetrahydro-imidazo[4,5-h]chromene;

2-Amino-3-cyano-4-(3-bromo-4,5-dimethoxyphenyl)-8-imino-4,7,8,9-tetrahydro-imidazo[4,5-h]chromene;

2-Amino-3-cyano-4-(3-methoxyphenyl)-imino-4,7,8,9-tetrahydro-imidazo[4,5-h]chromene;

2-Amino-3-cyano-4-(3-bromo-4,5-dimethoxyphenyl)-8-oxo-4,7,9-trihydro-2,1,3-thiadiazo[4,5-h]chromene;

2-Amino-3-cyano-4-(3-methoxyphenyl)-8-oxo-4,7,9-trihydro-2,1,3-thiadiazo[4,5-h]chromene;

2-Amino-3-cyano-4-(3-methoxyphenyl)-8-oxo-4,7,8-trihydro-oxazo[4,5-h]chromene;

2-Amino-3-cyano-4-(3-methoxyphenyl)-4H-oxazo[4,5-h]chromene;

2-Amino-3-cyano-4-(3-methoxyphenyl)4,7,8,9-tetrahydro-8,9-dioxo-oxazine[2,3-h]chromene;

2-Amino-3-cyano-4-(3-bromo-4,5-dimethoxyphenyl)-4,7,8,9-tetrahydro-8,9-dioxo-oxazine[2,3-h]chromene;

2-Amino-3-cyano-4-(3-bromo-4,5-dimethoxyphenyl)-4H-thiazo[4,5-h]chromene;

2-Amino-3-cyano-4-(3-methoxyphenyl)-4H-thiazo[4,5-h]chromene;

2-Amino-3-cyano-4-(3-bromo-4,5-dimethoxyphenyl)-4H-triazo[4,5-h]chromene;

2-Amino-3-cyano-4-(3-methoxyphenyl)-4H-triazo[4,5-h]chromene;

2-Amino-3-cyano-4-(3-bromo-4,5-dimethoxyphenyl)-8-oxo-4,8,9-trihydro-oxazo[5,4-h]chromene;

2-Amino-3-cyano-4-(3-bromo-4,5-dimethoxyphenyl)-8-oxo-4,8-dihydro-9-methyl-oxazo[5,4-h]chromene;

2-Methoxymethylimine-3-cyano-4-(3-bromo-4,5-dimethoxyphenyl)-4H-oxazo[5,4-h]chromene;

2-Amino-3-cyano-4-(3-bromo-4,5-dimethoxyphenyl)-8-oxo-4,7,8-trihydro-oxazo[4,5-h]chromene;

2-Amino-3-cyano-4-(3-bromo-4,5-dimethoxyphenyl)-8-oxo-4,8-dihydro-7-methyl-oxazo[4,5-h]chromene;

2-Amino-3-cyano-4-(3-bromo-4,5-dimethoxyphenyl)-4H-oxazo[4,5-h]chromene; and

2-Amino-3-cyano-4-(3-bromo-4,5-dimethoxyphenyl)-4H-oxazo[5,4-h]chromene.

21. The method of claim 12, wherein said compound has the Formula II:

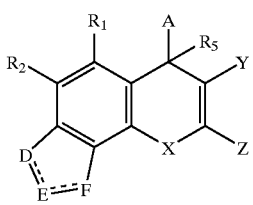

(II)

or pharmaceutically acceptable salts or prodrugs thereof, wherein

D, E, and F are $CR_{15}R_{16}$, CO, N, O, or S, wherein $R_{15}$ and $R_{16}$, are independently hydrogen or alkyl;

provided that at least two of D, E and F are hetero atoms and at least one of D, E and F is N; and the dashed line represents a single bond or a double bond, with the proviso that both the dashed lines can not be a double bond at the same time.

22. The method of claim 12, wherein said compound has the formula:

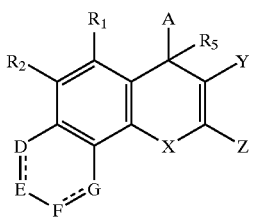

(III)

or pharmaceutically acceptable salts or prodrugs thereof, wherein $R_1$, $R_2$, $R_5$, X, Y, Z and A are as defined previously with respect to Formula I;

D, E, F, and G are $CR_{15}R_{16}$, CO, N, O, or S, wherein $R_{15}$ and $R_{16}$ are independently hydrogen or alkyl, provided that at least two of D, E, F, and G are hetero atoms and at least one of D, E, F and G is N; and the dashed lines represent a single bond or a double bond.

23. The method of claim 22, wherein said compound is 2-amino-3-cyano-4-(3-methoxyphenyl)4,7,8,9-tetrahydro-8,9-dioxo-oxazine[2,3-h]chromene; or
2-amino-3-cyano-4-(3-bromo-4,5-dimethoxyphenyl)4,7,8,9-tetrahydro-8,9-dioxo-oxazine[2,3-h]chromene.

24. The method of claim 12, wherein said disorder is cancer.

25. The method of claim 24, wherein said cancer is selected from the group consisting of Hodgkin's disease, non-Hodgkin's lymphoma, acute and chronic lymphocytic leukemias, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head and neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer and prostatic carcinoma.

26. The method of claim 24, wherein said cancer is a drug resistant cancer.

27. The method of claim 24, additionally comprising administering at least one known cancer chemotherapeutic agent, or a pharmaceutically acceptable salt of said agent.

28. The method of claim 27, wherein said known cancer therapeutic agent is selected from the group consisting of busulfan, cis-platin, mitomycin C, carboplatin, colchicine, vinblastine, paclitaxel, docetaxel, camptothecin, topotecan, doxorubicin, etoposide, 5-azacytidine, 5-fluorouracil, methotrexate, 5-fluoro-2'-deoxy-uridine, ara-C, hydroxyurea, thioguanine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Herceptin®, Rituxan® and alanosine.

29. The method of claim 24, additionally comprising treating with radiation therapy.

30. The method of claim 24, wherein said compound is administered after surgical treatment for cancer.

31. The method of claim 12, wherein said disorder is an autoimmune disease.

32. The method of claim 12, wherein said disorder is rheumatoid arthritis.

33. The method of claim 12, wherein said disorder is inflammation.

34. The method of claim 12, wherein said disorder is inflammatory bowel disease.

35. The method of claim 12, wherein said disorder is psoriasis.

36. The method of claim 12, wherein said disorder is a skin disease.

* * * * *